(12) United States Patent
Wyrick et al.

(10) Patent No.: US 11,891,414 B2
(45) Date of Patent: Feb. 6, 2024

(54) SAMPLE PLATES FOR BUFFER EXCHANGE AND METHODS OF MANUFACTURE

(71) Applicant: Unchained Labs, Pleasanton, CA (US)

(72) Inventors: David Wesley Wyrick, Pleasanton, CA (US); Stuart Kazumi Morita, Sunnyvale, CA (US); Lynn Comiskey, San Jose, CA (US); David Eugene Eberhart, Santa Clara, CA (US)

(73) Assignee: Unchained Labs, Pleasanton, CA (US)

( * ) Notice: Subject to any disclaimer, the term of this patent is extended or adjusted under 35 U.S.C. 154(b) by 505 days.

(21) Appl. No.: 15/927,934

(22) Filed: Mar. 21, 2018

(65) Prior Publication Data

US 2018/0273583 A1 Sep. 27, 2018

Related U.S. Application Data

(60) Provisional application No. 62/474,757, filed on Mar. 22, 2017.

(51) Int. Cl.
*B01L 3/00* (2006.01)
*C07K 1/34* (2006.01)
*C07K 16/00* (2006.01)
*B01D 61/14* (2006.01)
*B01D 61/02* (2006.01)
(Continued)

(52) U.S. Cl.
CPC .............. *C07K 1/34* (2013.01); *B01D 61/027* (2013.01); *B01D 61/145* (2013.01); *B01L 3/50255* (2013.01); *C07K 16/00* (2013.01); *G01N 1/34* (2013.01); *B01L 2300/0681* (2013.01); *B01L 2300/0829* (2013.01); *B01L 2300/0851* (2013.01); *G01N 2001/4088* (2013.01)

(58) Field of Classification Search
CPC ......... B01L 3/50255; B01L 2200/0689; B01L 2300/0681; B01L 2300/0829; B01L 2300/0851; G01N 2001/4088
See application file for complete search history.

(56) References Cited

U.S. PATENT DOCUMENTS

| 4,948,442 A | 8/1990 | Manns |
| 6,485,690 B1 * | 11/2002 | Pfost .................... B01J 19/0046 422/552 |

(Continued)

FOREIGN PATENT DOCUMENTS

| CA | 2949696 A1 | 11/2015 |
| JP | 2003-506456 A | 2/2003 |

(Continued)

OTHER PUBLICATIONS

International Search Report dated Jun. 20, 2018, for PCT Application No. PCT/US2018/023568, filed on Mar. 21, 2018, 2 pages.

(Continued)

*Primary Examiner* — Jill A Warden
*Assistant Examiner* — Dwayne K Handy
(74) *Attorney, Agent, or Firm* — COOLEY LLP (57) ABSTRACT

Sample plates and methods for exchanging buffer solutions are disclosed herein. The sample plates and methods may be used with automated buffer exchange systems where high pressures, for example, pressures of at least about 30 psig, are applied across a filtering membrane. Methods for manufacturing the sample plates are further disclosed.

12 Claims, 12 Drawing Sheets (51) Int. Cl.
    *G01N 1/34*       (2006.01)
    *G01N 1/40*       (2006.01)

(56)           References Cited

U.S. PATENT DOCUMENTS

| | | |
|---|---|---|
| 6,883,958 B2 | 4/2005 | Mayer |
| 2001/0012493 A1 | 8/2001 | Zermani |
| 2004/0012493 A1* | 1/2004 | Park .................. G08B 13/19 340/545.1 |
| 2004/0063169 A1 | 4/2004 | Kane |
| 2004/0144484 A1 | 7/2004 | Fisher |
| 2007/0098601 A1 | 5/2007 | Mabuchi et al. |
| 2007/0148649 A1 | 6/2007 | Shigesada et al. |
| 2011/0256025 A1 | 10/2011 | Mabuchi et al. |
| 2012/0329163 A1 | 12/2012 | Faber et al. |
| 2014/0298924 A1 | 10/2014 | Scott et al. |
| 2016/0016123 A1 | 1/2016 | Ishikawa et al. |

FOREIGN PATENT DOCUMENTS

| | | |
|---|---|---|
| JP | 2006-181567 A | 7/2006 |
| JP | 2010-036081 A | 2/2010 |
| WO | WO-2015/179598 | 11/2015 |
| WO | WO-2018175584 A1 | 9/2018 |

OTHER PUBLICATIONS

Written Opinion of the International Searching Authority dated Jun. 20, 2018, for PCT Application No. PCT/US2018/023568, filed on Mar. 21, 2018, 6 pages.

Extended European Search Report dated Sep. 29, 2020, for EP Application No. 18 772 039.6, filed on Mar. 21, 2018, 10 pages.

* cited by examiner

TEST PLATE #1 – SEAHORSE 30kDa (30 PSI)

| | 1 | 2 | 3 | 4 | 5 | 6 | 7 | 8 | 9 | 10 | 11 | 12 |
|---|---|---|---|---|---|---|---|---|---|---|---|---|
| A | | | | | | | x | x | | | | |
| B | | | | | x | x | | | | | | |
| C | | | | | x | | | | | | | |
| D | | | | x | x | | | x | | | | |
| E | | x | | | x | x | | | | | | |
| F | | | | | x | | | | | | | |
| G | | | | x | x | | x | | | x | x | |
| H | x | | | | x | x | x | x | x | x | | |

FIG. 6

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B | x |   |   |   |   |   | x |   |   | x  |    |    |
| C |   |   |   |   |   |   |   |   |   |    |    |    |
| D |   |   |   | x |   |   |   |   |   |    |    |    |
| E |   |   |   |   |   |   |   |   | x |    |    |    |
| F |   |   |   |   |   |   |   |   |   | x  |    |    |
| G |   |   |   |   |   |   |   |   |   |    |    |    |
| H | x |   |   |   |   |   |   |   |   |    |    |    |

TEST PLATE #2 – PALL ACROPREP™ ADVANCE 10kDa (30 PSI)

FIG. 7

TEST PLATE #3 – PALL ACROPREP™ ADVANCE 30kDa (30 PSI)

|   | 1 | 2 | 3 | 4 | 5 | 6 | 7 | 8 | 9 | 10 | 11 | 12 |
|---|---|---|---|---|---|---|---|---|---|----|----|----|
| A | x |   | x | x | x | x | x |   |   |    |    |    |
| B | x |   |   | x | x |   | x | x |   | x  |    |    |
| C |   | x | x |   | x | x |   |   |   |    | x  |    |
| D |   |   |   |   | x |   |   |   |   |    |    |    |
| E |   |   |   |   |   |   |   |   |   |    |    |    |
| F | x |   | x |   |   |   |   |   |   |    |    |    |
| G | x |   |   |   |   |   |   |   |   |    |    |    |
| H |   |   | x | x |   | x |   |   |   |    |    | x  |

FIG. 8

|  | 1 | 2 | 3 | 4 | 5 | 6 | 7 | 8 | 9 | 10 | 11 | 12 |
|---|---|---|---|---|---|---|---|---|---|---|---|---|
| A | x | x | x | x | x | x | x | x | x | x | x | x |
| B | x | x | x | x | x | x | x | x | x | x | x | x |
| C | x | x | x | x | x | x | x | x | x | x | x | x |
| D | x | x | x | x | x | x | x | x | x | x | x | x |
| E | x | x | x | x | x | x | x | x | x | x | x | x |
| F | x | x | x | x | x | x | x | x | x | x | x | x |
| G | x | x | x | x | x | x | x | x | x | x | x | x |
| H | x | x | x | x | x | x | x | x | x | x | x | x |

TEST PLATE #4 – ANALYTICAL SCIENCES 10kDa (60, 30, 15 PSI)

FIG. 9

SAMPLE PLATES FOR BUFFER EXCHANGE AND METHODS OF MANUFACTURE

CROSS-REFERENCE TO RELATED APPLICATIONS

This application claims priority to U.S. Provisional Application Ser. No. 62/474,757, filed Mar. 22, 2017, the disclosure of which is hereby incorporated by reference in its entirety.

FIELD

Described herein are sample plates and methods for exchanging buffer solutions for preparation of biological samples. The methods may include automated exchange of a buffer solution where high pressures are used to push the buffer solution through a reservoir filter of the plate. A filter attachment region may be provided that reinforces the seal of the filter to the reservoir such that the filter avoids detachment under this high level of pressure. Methods of manufacturing the sample plates are further described.

BACKGROUND

Biological components such as proteins are often formulated for further processing and analysis. Such biological components may be prepared as samples containing the biological component in a buffer solution, which maintains a relatively narrow pH range in which the component is biologically active and viable. Generally, buffer solutions are exchanged during downstream processing of the biological component. Such buffer exchange may be labor intensive, time-consuming, and inefficient as the biological component must be slowly exchanged into the new buffer via dilution and concentration cycles without altering the activity and viability of the biological component.

To decrease the amount of time spent on the buffer exchange process, automated systems for sample preparation have been developed. However, these systems typically employ high pressure differentials across the reservoir filter that may cause filter detachment in currently available sample plates. Accordingly, it would be beneficial to have sample plates suitable for use with fully automated buffer exchange systems.

SUMMARY

Described herein are sample plates for automated exchange of a buffer solution from a biological sample, methods of automated buffer exchange using the sample plates, and associated methods of manufacture. In general, the sample plates include a plurality of reservoirs, where each reservoir of the plurality of reservoirs comprises a side wall, a filter having a peripheral edge, and a filter attachment region. The filter attachment region may be reinforced to strengthen fixation of the filter to the reservoir wall to prevent filter separation therefrom when high pressure differentials are present across the filter, for example, at pressure differentials of at least about 30 psig.

In some variations, the sample plates for automated exchange of a buffer solution include a plurality of reservoirs, where each reservoir of the plurality of reservoirs comprises a side wall and a filter attachment region comprising a dual seal such as a thermal seal and an adhesive seal; and a filter having a peripheral edge secured to each reservoir at the filter attachment region, where the filter attachment region maintains fixation of the filter peripheral edge to each reservoir at a pressure differential across the filter of at least about 30 psig.

In other variations, the sample plates for automated exchange of a buffer solution include a plurality of reservoirs, where each reservoir of the plurality of reservoirs comprises a side wall and a filter attachment region comprising a thermal seal; and a filter having a peripheral edge secured to each reservoir at the filter attachment region, where the thermal seal comprises the filter peripheral edge captured between a portion of the sample plate and a reservoir cap, and where the filter attachment region maintains fixation of the filter peripheral edge to each reservoir at a pressure differential across the filter of at least about 30 psig.

Alternatively, the sample plates for automated buffer exchange may include a plurality of reservoirs, wherein each reservoir of the plurality of reservoirs comprises a side wall and a filter attachment region comprising a thermal seal; and a filter having a peripheral edge secured to each reservoir at the filter attachment region, where the thermal seal comprises the filter peripheral edge captured between a compressed O-ring and a portion of the sample plate, and where the filter attachment region maintains fixation of the filter peripheral edge to each reservoir at a pressure differential across the filter of at least about 30 psig.

Methods for the automated exchange of buffer solutions from biological sample are also described herein. The methods may generally include placing a sample plate comprising a plurality of reservoirs into a pressure chamber, where each reservoir of the plurality of reservoirs comprises a filter and a filter attachment region comprising a thermal seal and an adhesive seal; and pressurizing a space in the pressure chamber above the sample plate to generate a pressure differential across the filter of at least about 30 psig to separate the biological sample from a first buffer solution. Thereafter, a second buffer solution may be added to the plurality of reservoirs. Instead of the filter attachment region comprising a dual seal such as the thermal seal and adhesive seal mentioned above, the filter attachment region may comprise the filter peripheral edge captured between a portion of the sample plate and a reservoir cap, or the filter peripheral edge captured between a compressed O-ring and a portion of the sample plate.

Further described herein are methods of manufacturing sample plates for automated exchange of buffer solutions. The manufacturing methods may generally include loading a filter having a peripheral edge into a plurality of reservoirs, where each reservoir of the plurality of reservoirs comprises a side wall, a filter attachment region, and an inner ridge, the filter attachment region comprising a channel defined by the side wall and the inner ridge; thermally sealing the filter peripheral edge to the filter attachment region; and adhesively sealing the filter peripheral edge to the filter attachment region. Other manufacturing methods may only include creating a thermal seal where the filter peripheral edge is captured between a portion of the sample plate and a reservoir cap, or the filter peripheral edge is captured between a compressed O-ring and a portion of the sample plate.

BRIEF DESCRIPTION OF THE DRAWINGS

FIGS. 3A and 3B depict a filter attachment region according to another variation.

FIGS. 4A and 4B depict a filter attachment region according to a further variation.

DETAILED DESCRIPTION

Described herein are sample plates and methods for automated exchange of buffer solutions during preparation of biological samples. The sample plates may be beneficial when automated exchange of a buffer solution includes the use of high pressure differentials across a reservoir filter of the plate, for example, when protein samples are highly concentrated. The sample plates may comprise a filter attachment region for reinforcing the attachment of the filter to the reservoir such that the filter remains secured to the reservoir under this high level of pressure. Methods of manufacturing the sample plates are further described.

Sample Plates

Figure 1:
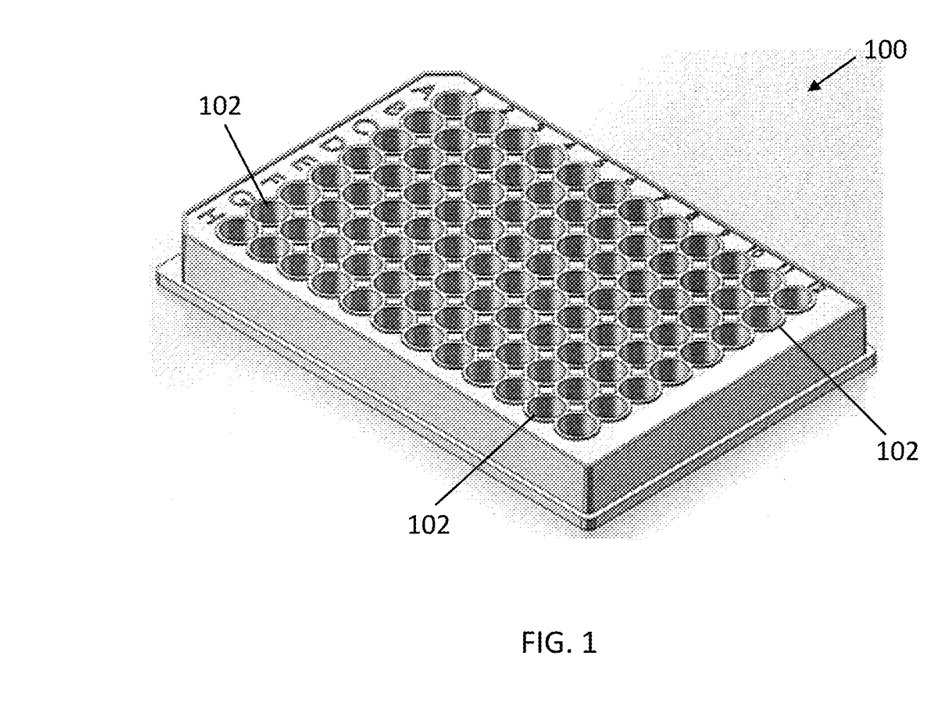
FIG. 1 is a perspective view of a sample plate according to one variation.

In general, the sample plates include a plurality of reservoirs, where each reservoir of the plurality of reservoirs comprises a side wall, a filter having a peripheral edge, and a filter attachment region. The sample plates may be used to prepare samples of biological components such as proteins, peptides, antigens, antibodies, enzymes, microorganisms, DNA, RNA, and the like, for further analysis. The sample plates may include any suitable number of reservoirs desired for processing the biological component. For example, the sample plates may include one reservoir, or a plurality of reservoirs, such as at least 2, at least 3, at least 4, at least 5, at least 6, at least 10, at least 12, at least 16, at least 24, at least 48, or at least 96 reservoirs. The volume of the reservoirs may be about 75 ml or less or, in other variations, about 25 ml or less, about 16 ml or less, about 8 ml or less, about 4 ml or less, about 1 ml or less, about 750 µl or less, about 500 µl or less, or about 250 µl or less. Referring to FIG. 1, an exemplary sample plate (100) containing 96 reservoirs (102) is shown. The sample plates may be made from plastic materials including, but not limited to, acrylonitrile butadiene styrene (ABS), poly-styrene (PS), polypropylene (PP), polycarbonate (PC), and glass-reinforced nylon (GFN).

Generally, each reservoir comprises a filter that forms part of the bottom of the reservoir, and which allows separation of the biological component from the buffer solution during use. The filters may be die cut to a size and shape suitable for use with the intended reservoir. The filter typically has a pore size less than the size of the biological component(s) desired to be retained in the reservoirs. Depending on the biological component, the filter may be an ultrafiltration or a nanofiltration-sized filter. In some variations, the filter may have a molecular weight cutoff of about 3 kDa, about 10 kDa, about 30 kDa, or about 100 kDa.

Upon pressurizing the reservoirs, a pressure difference forms across the filter to force buffer solution through the filter to produce a concentrated solution of protein in the reservoir. As previously stated, high pressures may be used when the buffer exchange process is automated and/or the buffer solution from highly concentrated samples is being forced through the filter by pressurization above the filter. These pressure differences are typically higher than that generated during filtration by centrifugation, which is about 15 psig. Accordingly, the reservoirs described herein may be pressurized such that a pressure differential of at least about 30 psig, at least about 35 psig, at least about 40 psig, at least about 45 psig, at least about 50 psig, at least about 55 psig, at least about 60 psig, at least about 65 psig, at least about 75 psig, at least about 80 psig, at least about 85 psig, at least about 90 psig, at least about 95 psig, or at least about 100 psig is formed across the filter and used to remove filtrate. In some variations, the pressure differential ranges from about 30 psig to about 60 psig. In other variations, the pressure differential employed is about 60 psig. In order to prevent all or partial detachment of the filter from the reservoir under these high pressure differentials, the sample plates described herein may comprise various filter attachment regions that reinforce filter attachment to the reservoir.

In some variations, the sample plate for automated exchange of a buffer solution from a biological sample includes a plurality of reservoirs, where each reservoir of the plurality of reservoirs comprises a side wall and a filter attachment region comprising a dual seal such as a thermal seal and an adhesive seal; and a filter having a peripheral edge secured to each reservoir at the filter attachment region, where the filter attachment region maintains fixation of the filter peripheral edge to each reservoir at a pressure differential across the filter of at least about 30 psig.

When a thermal seal is employed, thermoplastic staking, also known as heat staking, may be used to secure the filter to the reservoir by the application of heat and force. Force may be applied first to optimize contact of the filter to the filter attachment region. Heat may then be used to soften the material in the filter attachment region and attach the filter to the reservoir. Other techniques for thermally joining materials may also be used.

Figure 2A:
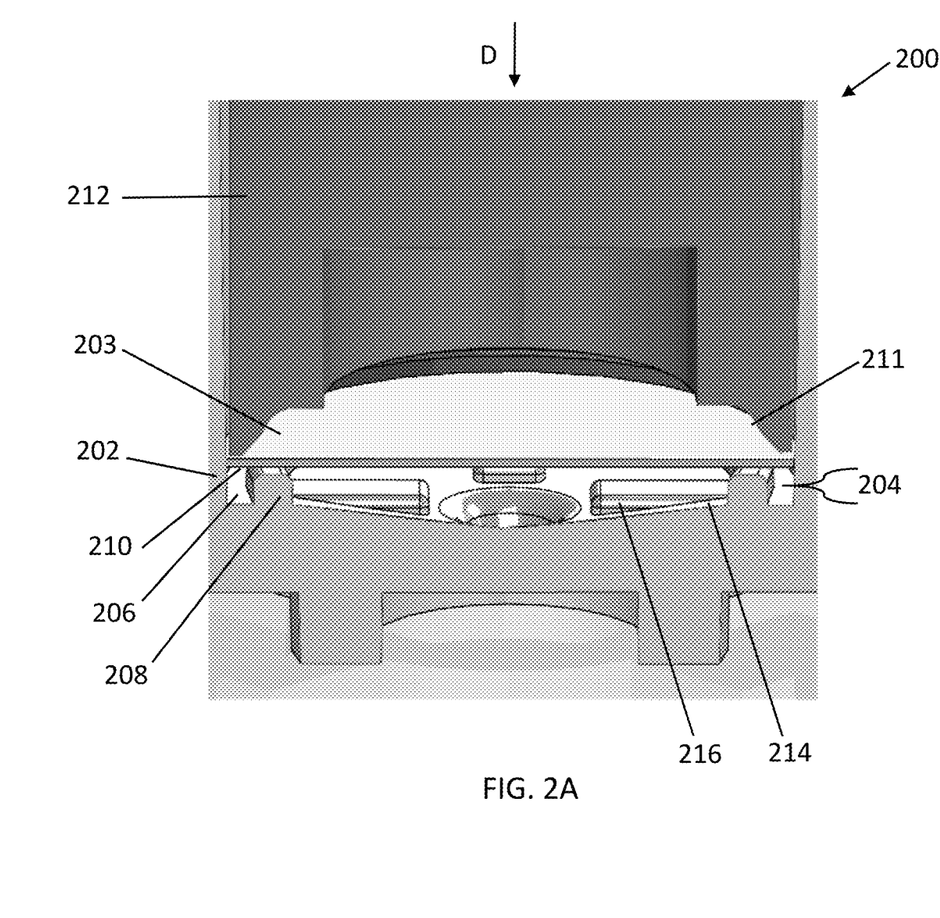
FIGS. 2A and 2B are cross-sectional views of a filter attachment region and method of filter attachment comprising a dual seal (thermal seal and adhesive seal) according to one variation.
Figure 2B:
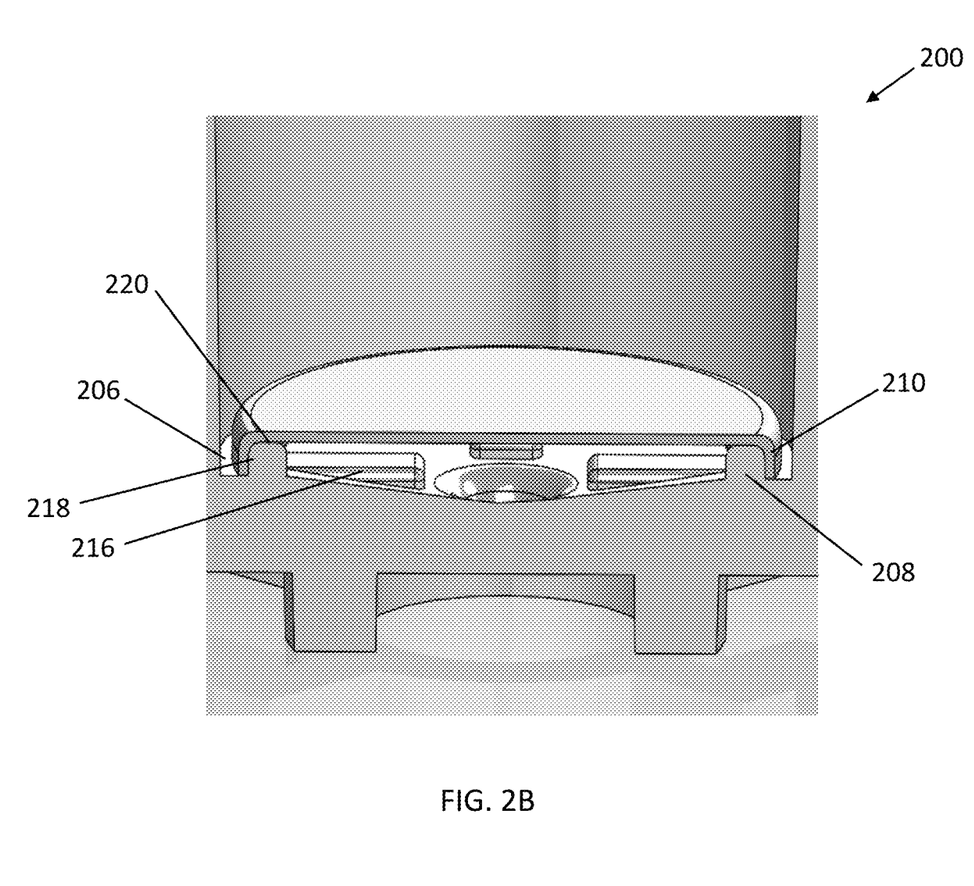

Referring to FIGS. 2A-2B, an exemplary filter attachment region of the reservoirs and method of forming the filter attachment region are illustrated. In FIG. 2A, reservoir (200) includes a side wall (202), a filter (203), and a filter attachment region (204). The filter attachment region (204) comprises a channel (206) defined by side wall (202) and an inner ridge (208) of reservoir (200). Attachment of the filter (203) to the inner ridge (208) is accomplished using a dual seal (thermal seal and adhesive seal), by initially applying force toward the reservoir floor (214) in the direction of arrow D to a peripheral edge (210) of filter (203) using a heated boss or heat stake (212). This downward force folds the peripheral edge (210) against inner ridge (208). Heat is then applied to the inner ridge (208) via heat stake (212) to soften the material of the inner ridge (208) and secure the filter peripheral edge (210) thereto. Upon attachment, the filter peripheral edge (210) in its folded configuration is attached to both the side (218) of the inner ridge (208) and top (220) of the inner ridge (208). The thermal seal formed in this manner is shown in FIG. 2B. The distal end of the heat stake may be shaped to approximate or match the contour of the area where materials are to be joined. In FIG. 2A, the distal end (211) of heat stake (212) is shaped to approximate the contour of inner ridge (208). Inner ridge (208) may be a ring or rim that continuously extends about the inner surface of side wall (202).

Next, an adhesive seal is formed by filling channel (206) with an adhesive and then curing the adhesive with UV light. Suitable adhesives may include those that do not leach components into the liquid samples after curing, or which are non-fluorescing. Upon pressurization from above, the filter may flex toward the reservoir bottom. Thus, the reservoirs may further include one or more filter supports (216) to decrease the force on the filter attachment region during pressurization.

The height of the inner ridge may vary depending on the pressure differential being generated across the filter. In general, the height of the inner ridge may range from about 0.25 mm to about 0.4 mm. For example, the inner ridge height may be about 0.25 mm, about 0.30 mm, about 0.35 mm, about 0.36 mm, about 0.37 mm, about 0.38 mm, about 0.39 mm, or about 0.40 mm. In some variations, the height of the inner ridge is about 0.38 mm (0.015 inch).

The diameter of the filter may also vary depending on the pressure differential being generated across the filter and the type of filter attachment region being used. For example, the filter diameter may be about 0.77 mm (about 0.03 inch). In some variations, the diameter of the filter and the height and width of the inner ridge are matched so that once the filter peripheral edge is attached to the top and sides of the inner ridge, it lies flat and the edges of the filter do not fold back up. This may provide maximum surface area for the adhesive to bond to the reservoir side wall and to the filter peripheral edge when creating the adhesive seal.

Referring to the Examples, the comparative study described in Example 1 demonstrated that the dual seal sample plate was compatible for use with an automated buffer exchange system employing high levels of pressurization, for example, pressurization of at least about 30 psig, or at least about 60 psig, and superior to commercially available plates, for example, the Seahorse™ 30 kDa microplate (Agilent Technologies, Chicopee, MA), the Acroprep™ Advance 10 kDa MWCO plate (Pall Corporation, Port Washington, NY), the Acroprep™ Advance 30 kDa MWCO plate (Pall Corporation, Port Washington, NY), and a 10 kDa MWCO filter plate from Analytical Sciences (Flanders, NJ). The study described in Example 2 further demonstrated that the dual seal sample plate may be used to buffer exchange highly concentrated protein samples, as well as buffer exchange the samples with minimal loss of the sample protein, which may be useful during the biopharmaceutical formulation process.

Figure 3A:
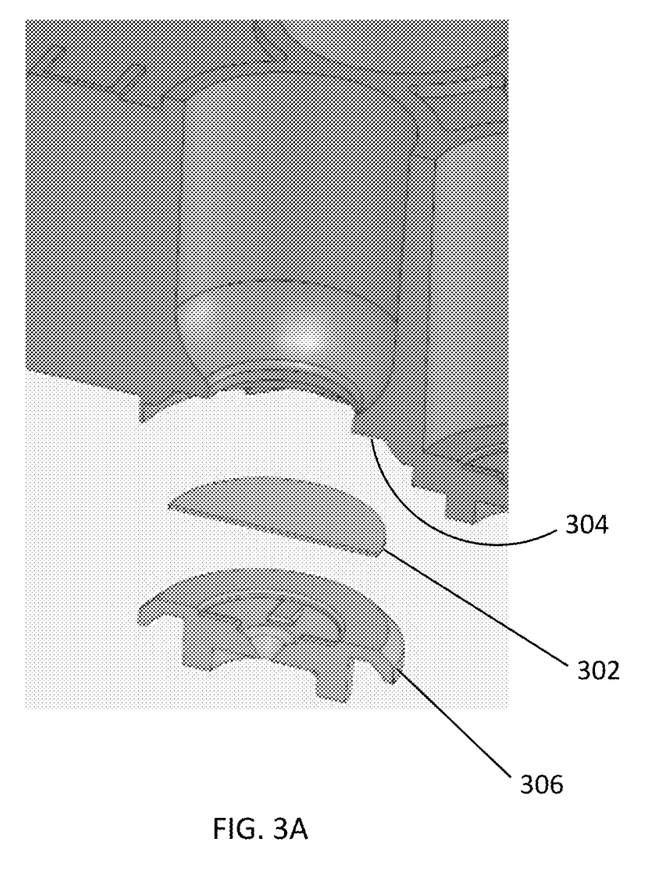
FIG. 3A shows the individual components of the filter attachment region.
Figure 3B:
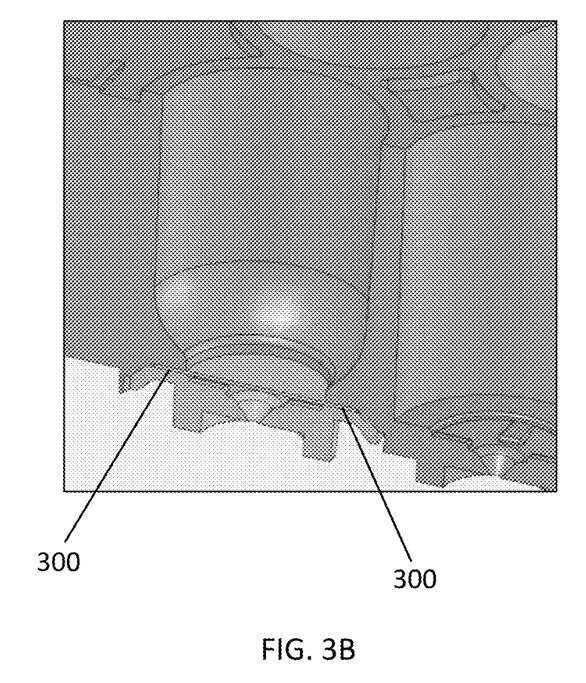
FIG. 3B shows a cross-sectional view of the filter attachment region after the individual components have been sealed together.

In other variations, the sample plate for automated exchange of a buffer solution from a biological sample includes a plurality of reservoirs, where each reservoir of the plurality of reservoirs comprises a side wall and a filter attachment region comprising a thermal seal; and a filter having a peripheral edge secured to each reservoir at the filter attachment region, where the thermal seal comprises the filter peripheral edge captured between a portion of the sample plate and a reservoir cap, and where the filter attachment region maintains fixation of the filter peripheral edge to each reservoir at a pressure differential across the filter of at least about 30 psig. In these variations, the thermal seal is also formed by heat staking. However, instead of applying force and heat to the top surface of the filter (retentate side of the filter), they are applied from below the filter, from the bottom of the sample plate. For example, as shown in FIGS. 3A and 3B, a thermal seal (300) (FIG. 3B) is formed by capturing the peripheral edge of filter (302) between a portion of the sample plate (304) and a reservoir cap (306), and fusing them together by applying pressure and heat against the reservoir cap (306) using an appropriately shaped heat stake (not shown).

Alternatively, the sample plate for automated exchange of a buffer solution from a biological sample includes a plurality of reservoirs, where each reservoir of the plurality of reservoirs comprises a side wall and a filter attachment region comprising a thermal seal; and a filter having a peripheral edge secured to each reservoir at the filter attachment region, where the thermal seal comprises the filter peripheral edge captured between a compressed O-ring and a portion of the sample plate, and where the filter attachment region maintains fixation of the filter peripheral edge to each reservoir at a pressure differential across the filter of at least about 30 psig.

Figure 4A:
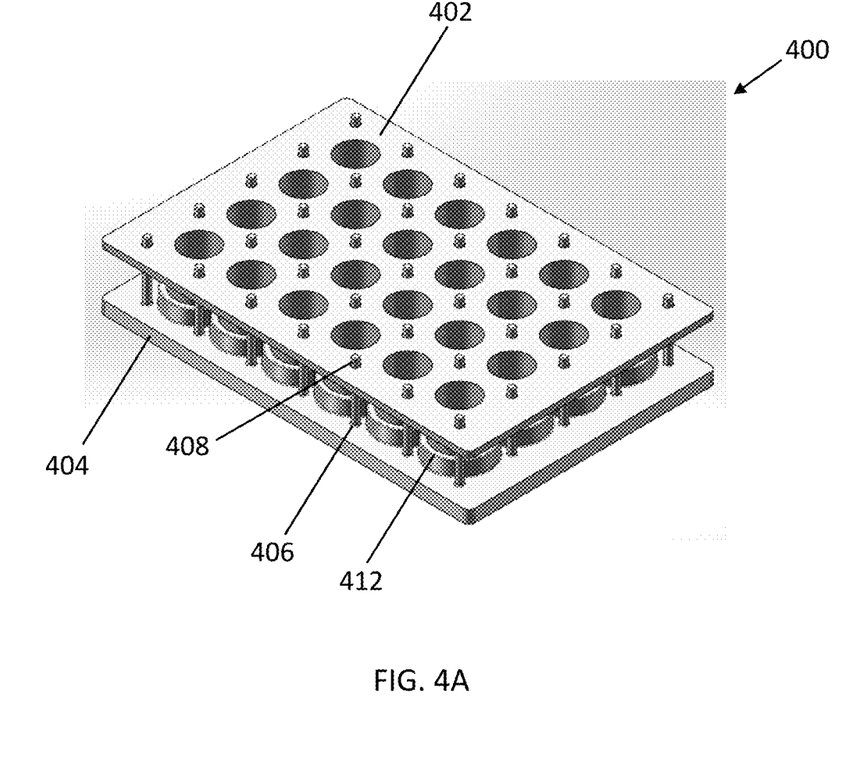
FIG. 4A shows the individual components of the filter attachment region.
Figure 4B:
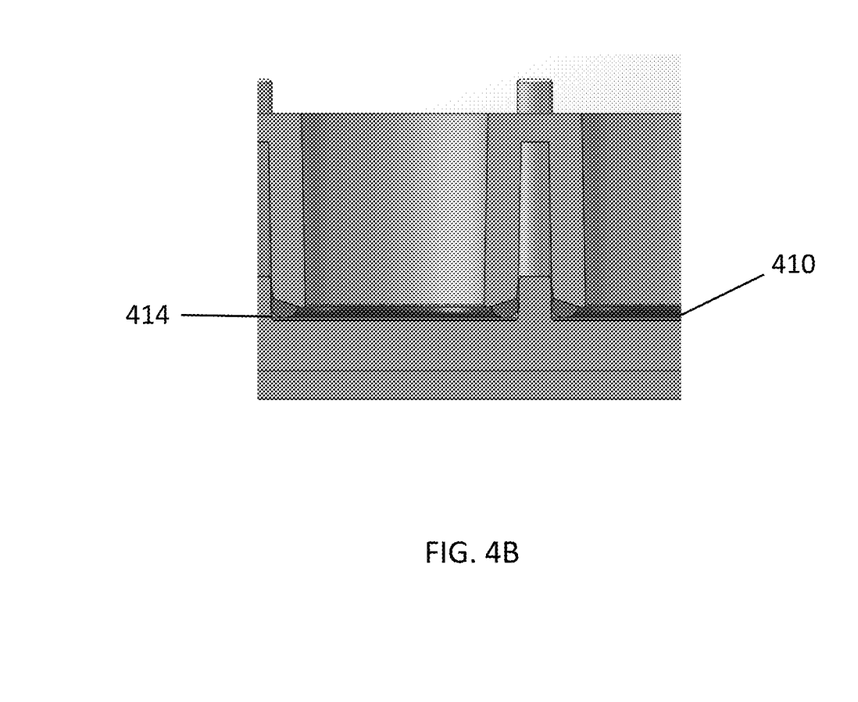
FIG. 4B shows an expanded, cross-sectional view of the filter attachment region after the individual components have been sealed together.

In variations where an O-ring is used, it may first be mechanically compressed and then portions of the sample plate thermally sealed to sandwich it between them such that the seal keeps the O-ring in its compressed configuration on top of the filter. In this variation, the sample plate may include an upper sealing plate and a lower support plate. For example, as shown in FIGS. 4A and 4B, sample plate (400) comprises an upper sealing plate (402) and a lower support plate (404) including connecting posts (406). Connecting posts (406) may be threaded through corresponding openings (408) in upper sealing plate (402). The number of connecting posts may vary as desired. An O-ring (410) is provided for each reservoir (412) between the upper sealing plate (402) and lower support plate (404). To make the sample plate, the upper sealing plate (402) and lower support plate (404) are pressed together by an array of heat stakes (not shown) to mechanically compress the O-ring (410) and sandwich the O-ring (410) and filter (414) between the plates. The heat stakes are then heated to form a thermal seal (see FIG. 4B) comprising the compressed O-ring (410) and filter (414) between the bonded upper sealing plate (402) and lower support plate (404). This variation of the filter attachment region may be useful when it is desired to interchange filters (prior to heat staking) to facilitate different molecular weight cutoffs.

The sample plates described herein may be used with the automated buffer exchange module of the Freeslate® system (Unchained Labs, Pleasanton, CA), and the automated buffer exchange methods and systems provided in International Application No. PCT/US2015/031900 (International Publication No. WO/2015/179598), entitled "SYSTEMS AND METHODS FOR EXCHANGE OF BUFFER SOLUTIONS," filed May 21, 2015, the contents of which are hereby incorporated by reference in their entirety. More specifically, the sample plates may be placed in the pressurization chamber of a filtration unit or buffer exchange module of the system, which forms an air-tight seal with the reservoirs. The buffer exchange module may be pressurized to generate a pressure differential across the filter of at least about 30 psig, or at least about 60 psig, that forces a first buffer solution through the filter and out of the reservoirs. The pressurization may be achieved by injecting air or an inert gas such as nitrogen into the reservoirs (e.g., by pressurizing the space above the reservoirs) to push the first buffer solution through the filter, leaving behind the biological component in the reservoir. A second buffer solution may then be introduced into the reservoirs. The buffer solutions that are exchanged may be the same or different. This cycle of buffer exchange can be repeated any suitable number of times, and any suitable type of buffer solution may be employed.

The sample plates may be used in various processes where automated buffer exchange is desired, for example, when biological components including, but not limited to, proteins, peptides, antigens, antibodies, enzymes, microorganisms, DNA, and RNA, are being formulated for further processing and analysis.

Buffer Exchange Methods

Methods for the automated exchange of buffer solutions from biological sample are also described herein. The methods may generally include placing a sample plate comprising a plurality of reservoirs into a pressure chamber, wherein each reservoir of the plurality of reservoirs comprises a filter and a filter attachment region comprising a thermal seal and an adhesive seal; and pressurizing a space in the pressure chamber above the sample plate to generate a pressure differential across the filter of at least about 30 psig to separate the biological sample from a first buffer solution. Thereafter, a second buffer solution may be added to the plurality of reservoirs. Instead of the filter attachment region comprising dual seal such as the thermal seal and adhesive seal mentioned above, the filter attachment region may comprise the filter peripheral edge captured between a portion of the sample plate and a reservoir cap, or the filter peripheral edge captured between a compressed O-ring and a portion of the sample plate.

Upon pressurizing the reservoirs, a pressure difference forms across the filter to force buffer solution through the filter thereby producing a buffer-depleted residue in the reservoir. As previously stated, high pressures may be used when the buffer exchange process is automated and the buffer solution is being forced through the filter by pressurization above the filter. These pressure differences are typically higher than that generated during filtration by centrifugation, which is about 15 psig. Accordingly, the reservoirs described herein may be pressurized such that a pressure differential of at least about 30 psig, at least about 35 psig, at least about 40 psig, at least about 45 psig, at least about 50 psig, at least about 55 psig, at least about 60 psig, at least about 65 psig, at least about 75 psig, at least about 80 psig, at least about 85 psig, at least about 90 psig, at least about 95 psig, or at least about 100 psig is formed across the filter and used to remove filtrate. In some variations, the pressure differential ranges from about 30 psig to about 60 psig. In other variations, the pressure differential employed is about 60 psig. The pressurization may be achieved by injecting air or an inert gas such as nitrogen into the reservoirs (e.g., by pressurizing the space above the reservoirs) to push the first buffer solution through the filter, leaving behind the biological component in the reservoir.

Filtration may occur using a filter that has a pore size less than the size of the biological component desired to be retained in the reservoirs, as previously stated. For example, if proteins have a size of 20 kDa or more, then pore sizes of less than 20 kDa would be used to retain the protein. Depending on the biological component, the filter may be an ultrafiltration or a nanofiltration-sized filter. In some variations, the filter may have pore sizes of about 1000 kDa or less, about 100 kDa or less, or about 10 kDa or less.

After filtration, a second buffer solution may be introduced into the reservoirs. The buffer solutions that are exchanged may be the same or different. This cycle of buffer exchange can be repeated any suitable number of times, and any suitable type of buffer solution may be employed. The buffer exchange methods may be useful when preparing biopharmaceutical formulations containing, for example, proteins, peptides, antigens, antibodies, enzymes, microorganisms, DNA, RNA, and the like.

Manufacturing

Methods of manufacturing sample plates for automated exchange of buffer solutions are further described herein. The manufacturing methods may generally include loading a filter having a peripheral edge into a plurality of reservoirs, wherein each reservoir of the plurality of reservoirs comprises a side wall, a filter attachment region, and an inner ridge, the filter attachment region comprising a channel defined by the side wall and the inner ridge; thermally sealing the filter peripheral edge to the filter attachment region; and adhesively sealing the filter peripheral edge to the filter attachment region. Other manufacturing methods may only include creating a thermal seal where the filter peripheral edge is captured between a portion of the sample plate and a reservoir cap, or the filter peripheral edge is captured between a compressed O-ring and a portion of the sample plate. In variations where an O-ring is used, it may first be mechanically compressed and then portions of the sample plate thermally sealed to sandwich it between them such that the seal keeps the O-ring in its compressed configuration on top of the filter.

Each reservoir of the plurality of reservoirs in the sample plate is loaded with a die cut filter. The filter edge or peripheral edge may then be thermally bonded to each reservoir to create a thermal seal. The filter peripheral edge may be folded to a folded configuration and then thermally bonded to each reservoir, or the filter peripheral edge may be thermally bonded to the reservoir in its unfolded configuration. In some variations, the filter is thermally bonded to each reservoir by heat staking, as previously described herein. The heat stakes may have a distal end that is shaped to direct heat to the appropriate area and/or to approximate or match the contour of the area to which the filter is being joined, as shown in FIG. 2A. However, the shape of the distal end of the heat stake is not limited to the shape provided in FIG. 2A, and may have any shape suitable for the intended area of use.

When a dual seal is employed, as shown in FIG. 2B, an adhesive moat is also created by injecting or otherwise filling a reservoir channel with a suitable adhesive after the filter edge has been thermally joined to the reservoir. The adhesive is then cured using UV light to create an adhesive seal. Filter attachment regions employing a dual seal may be useful when pressure differentials across the filter are equal to or greater than about 30 psig, or equal to or greater than about 60 psig.

In other variations, the filter attachment region is formed by only creating a thermal seal. The filter peripheral edge may be folded to a folded configuration and then thermally bonded to each reservoir, or the filter peripheral edge may be thermally bonded to the reservoir in its unfolded configuration. Heat stakes may be used to form the thermal seal, as described above. In some variations, as shown in FIGS. 3A-3B, the thermal seal is created by capturing a filter peripheral edge between a portion of the sample plate and a reservoir cap, and then thermally joining the portion of the sample plate and reservoir cap by heat staking. In another variation, the thermal seal is formed by pressing together a sealing plate and a support plate, which captures the filter peripheral edge between a compressed O-ring and the plates, and then thermally joining the sealing plate and the support plate, as illustrated in FIGS. 4A-4B.

EXAMPLES

The following examples further illustrate the sample plates and methods as disclosed herein, and should not be construed in any way as limiting their scope.

Example 1

Comparative Testing of Dual Seal Sample Plate and Commercially Available Plates

Sample plates capable of withstanding high pressurization, for example, pressurization of at least about 30 psig, or at least about 60 psig, may be useful in facilitating buffer exchange of biological samples at higher protein concentrations since these samples are generally more viscous.

A sample plate having a 10 kDa filter and filter attachment region comprising a dual seal (thermal seal and adhesive seal), as described herein, was tested against the following four commercially available plates: the Seahorse™ 30 kDa microplate (Agilent Technologies, Chicopee, MA), the Acroprep™ Advance 10 kDa MWCO plate (Pall Corporation, Port Washington, NY), the Acroprep™ Advance 30 kDa MWCO plate (Pall Corporation, Port Washington, NY), and a 10 kDa MWCO filter plate from Analytical Sciences (Flanders, NJ).

10 mg/ml IgG was pipetted into each reservoir of the plates. Each plate was placed into the buffer exchange module of the automated Freeslate® system (Unchained Labs, Pleasanton, CA) and then tested for reservoir failure, which was indicated by loss of all protein solution during pressurization. Separation of the filter from the reservoirs could also be easily visualized. The plates were first tested at a pressure differential (pressurization) of 60 psig across the filter since that level of pressurization may be useful in automated buffer exchange systems. If all the reservoirs failed at that pressure (total failure), then a new plate was tested at a pressurization of 30 psig. If total failure resulted at 30 psig, then a new plate was tested at a pressurization of 15 psig, which is the pressure differential generated with centrifuge-type buffer exchange systems. Pressurization was carried out for about 5 to about 30 minutes, depending on the plate being tested. Each reservoir was tracked, and marked with an "x" if there was total failure after pressurization.

Figure 5:
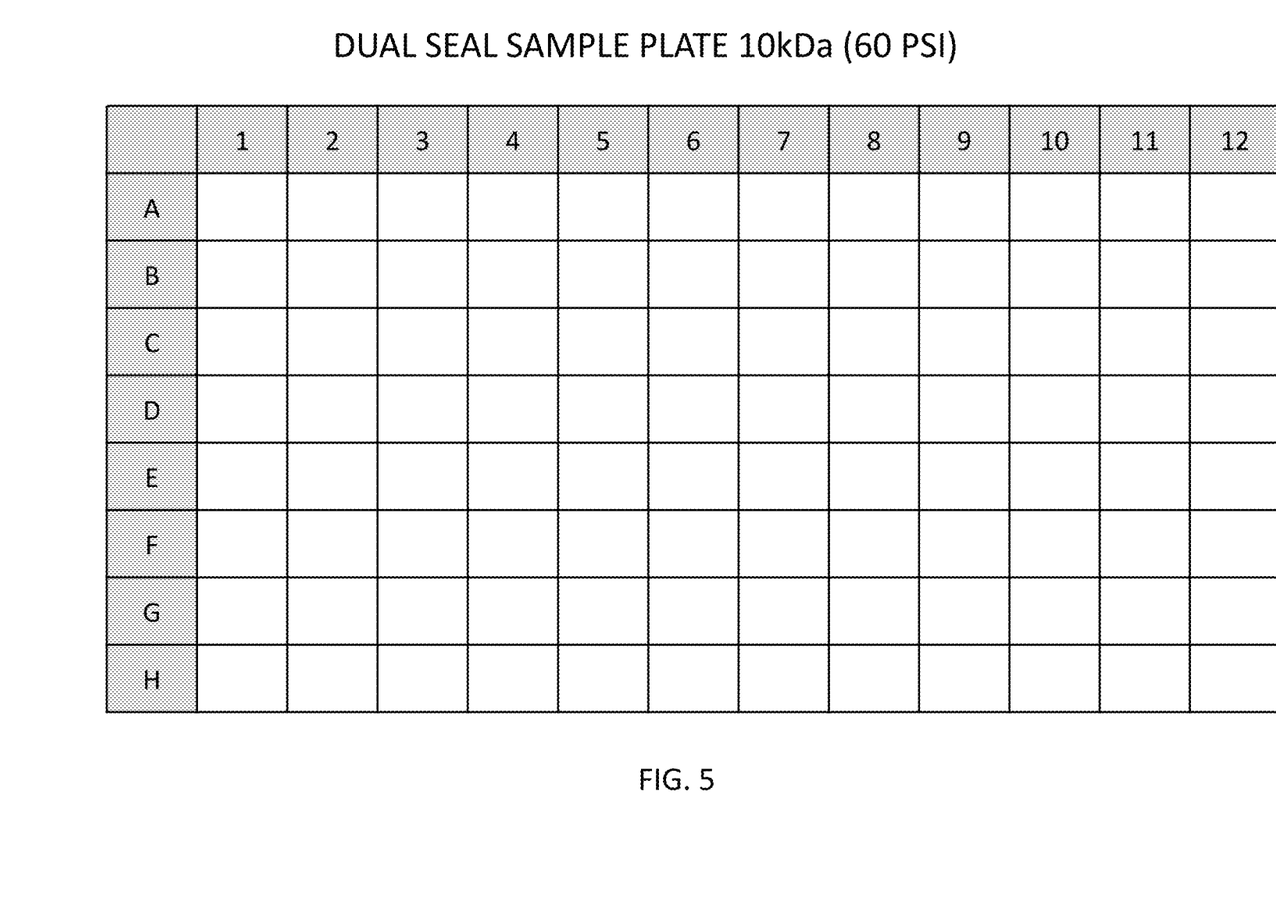
FIG. 5 shows data obtained from testing a dual seal sample plate at a pressure of 60 psig.
Figure 6:
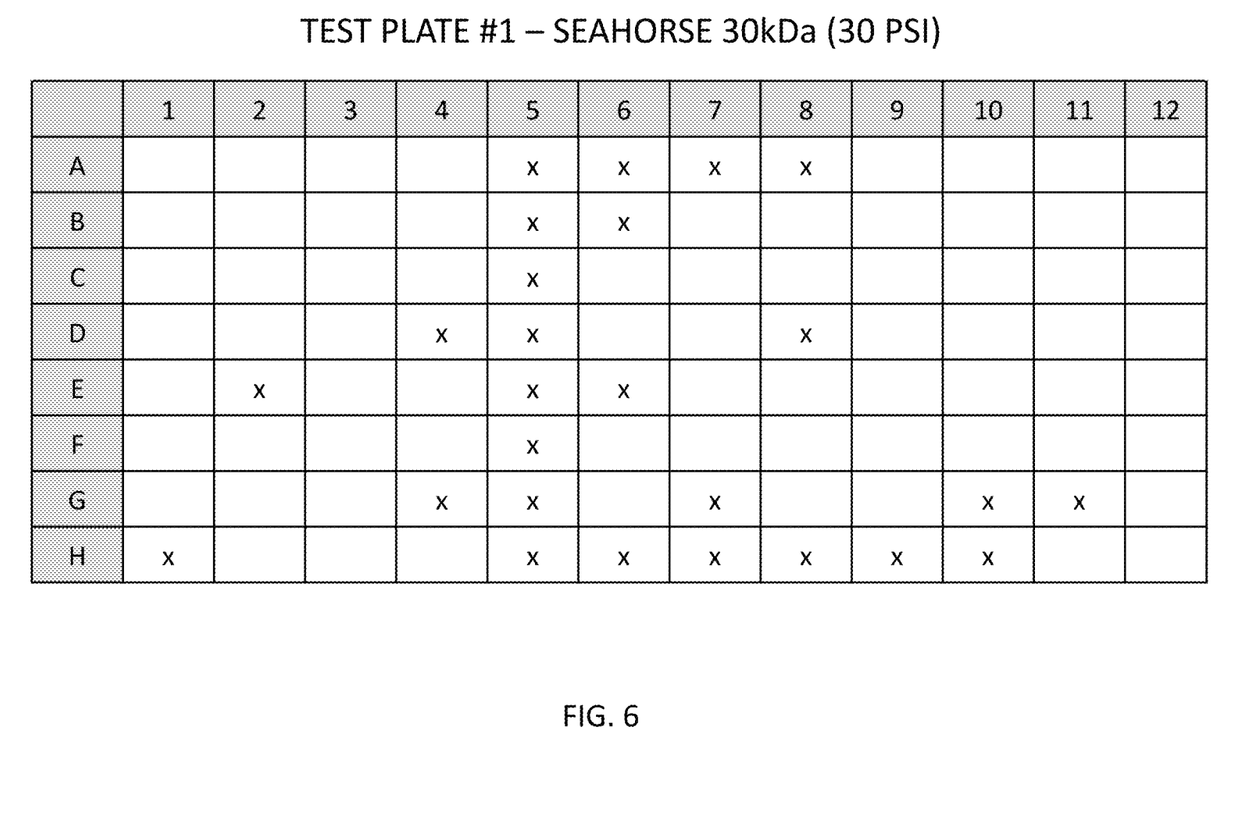
FIG. 6 shows data obtained from testing the Seahorse™ 30 kDa microplate at a pressure of 30 psig.
Figure 7:
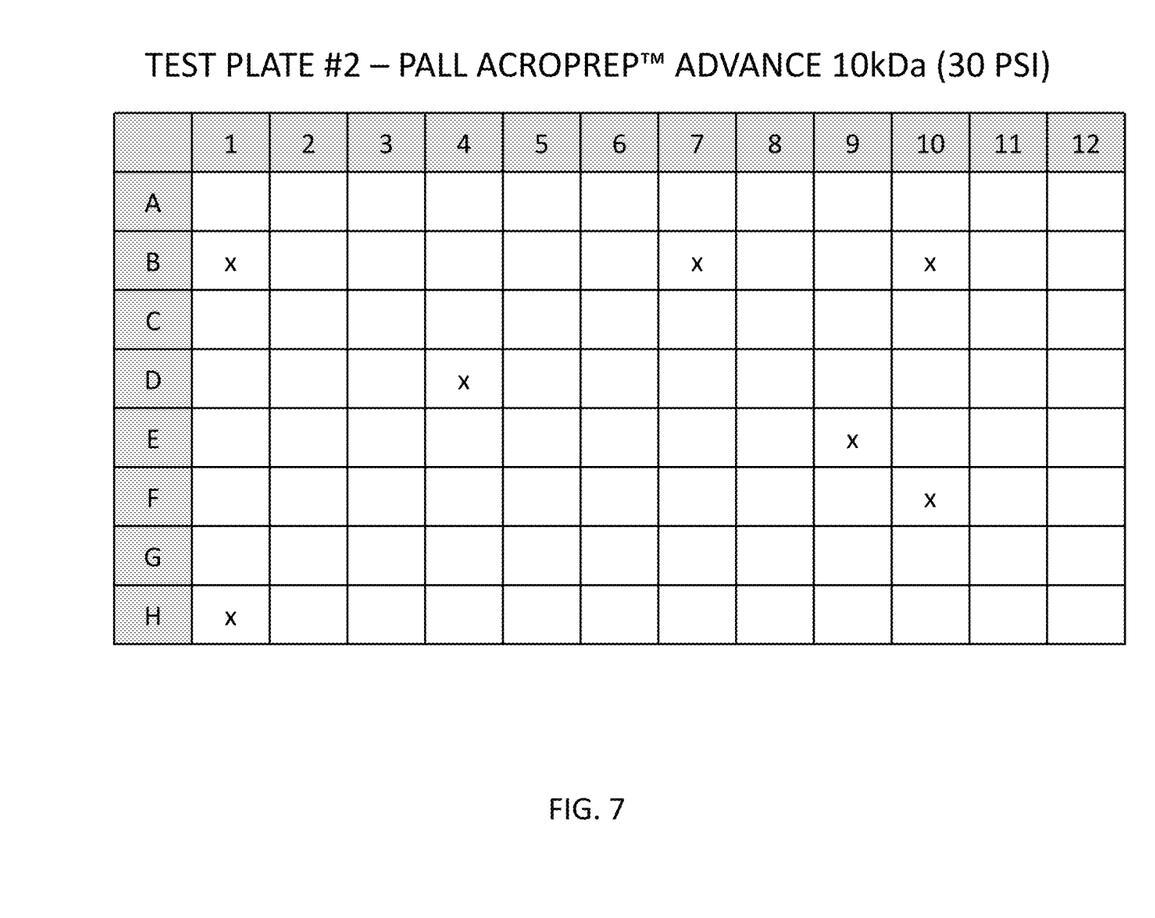
FIG. 7 shows data obtained from testing the Acroprep™ Advance 10 kDa MWCO plate at a pressure of 30 psig.
Figure 8:
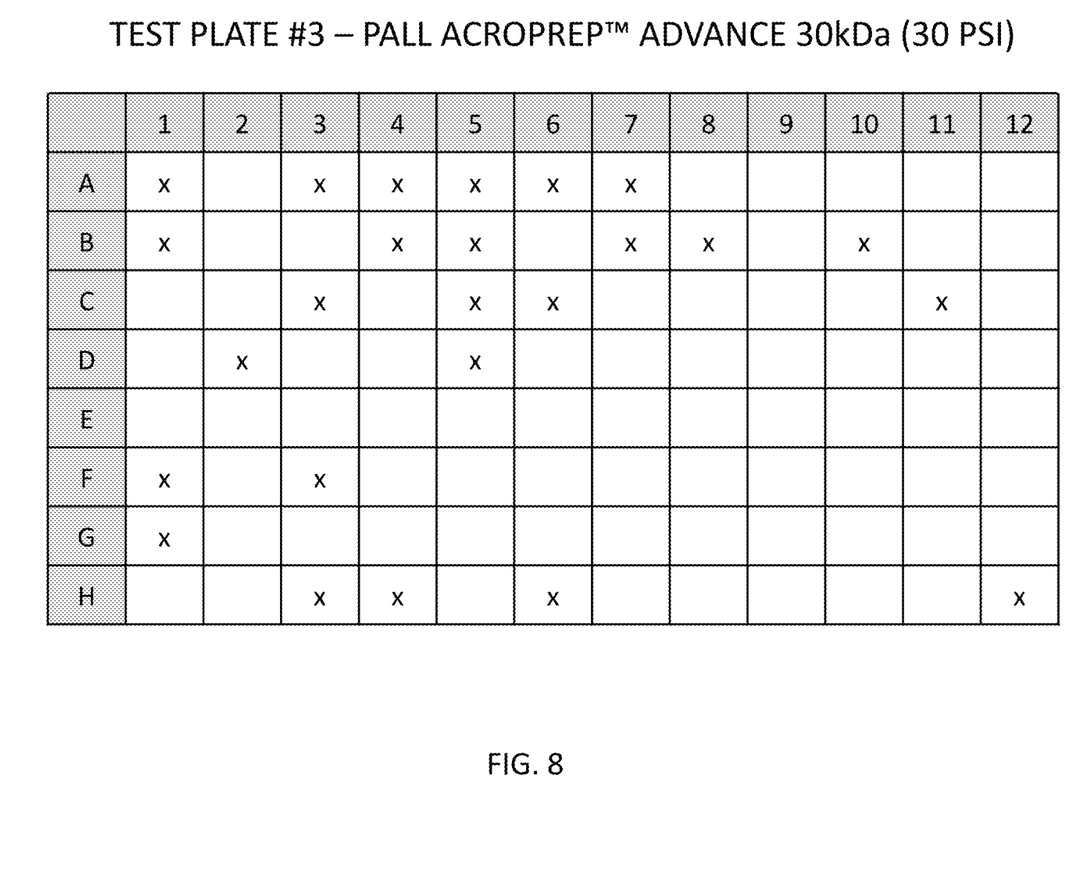
FIG. 8 shows data obtained from testing the Acroprep™ Advance 30 kDa MWCO plate at a pressure of 30 psig.
Figure 9:
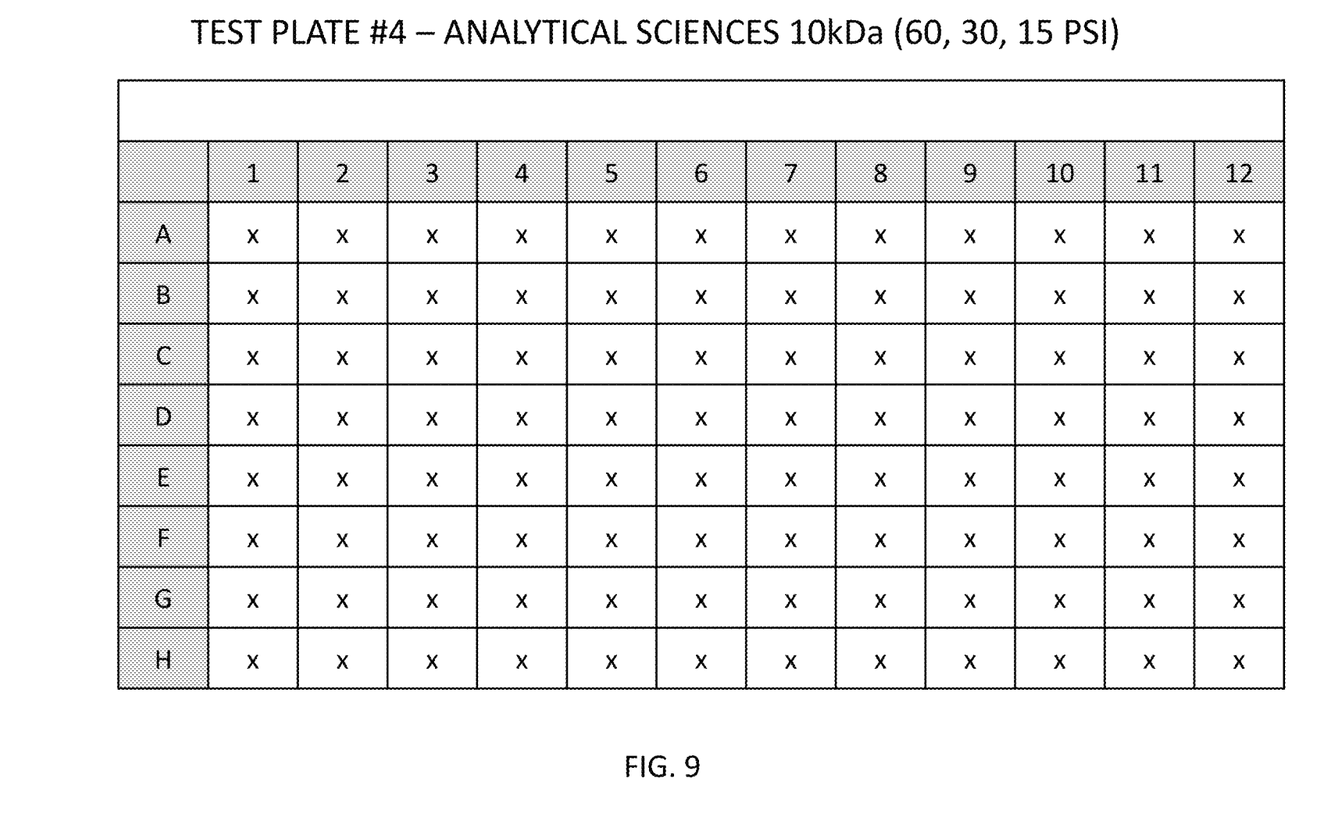
FIG. 9 shows data obtained from testing the Analytical Sciences 10 kDa MWCO filter plate at pressures of 60, 30, and 15 psig.

As shown in FIG. 5, the dual seal sample plate had no reservoir failures at 60 psig. In contrast, there was total failure of all reservoirs at 60 psig for the commercially available plates. At 30 psig, 26 reservoirs totally failed in the Seahorse™ 30 kDa microplate (FIG. 6), 7 reservoirs totally failed in the Pall Acroprep™ Advance 10 kDa MWCO plate (FIG. 7), and 25 wells totally failed in the Pall Acroprep™ Advance 30 kDa MWCO plate (FIG. 8). FIG. 9 depicts the 10 kDa MWCO plate by Analytical Sciences, in which total failure also occurred at 30 psig and 15 psig. The results obtained from the comparative testing indicated that the dual seal sample plate was compatible for use with an automated buffer exchange system employing high levels of pressurization, for example, pressurization of at least about 30 psig, or at least about 60 psig, and superior to commercially available plates.

Example 2

Protein Recovery of Buffer Exchanged High Concentration Samples

In addition to reservoir failure, protein recovery of high concentration protein samples was assessed for a dual seal sample plate, as described herein, having a 10 kDa filter. Here each reservoir of a 96-reservoir dual seal sample plate was loaded with a 100 mg/ml IgG sample. The sample plate was then placed in the buffer exchange module of the automated Freeslate® system (Unchained Labs, Pleasanton, CA). At 15 psig, the system stalled and was not able to exchange buffers. However, after a 24 hour run in which pressurization of 60 psig was used for buffer exchange, there were no reservoir failures and recovery of input protein of at least 92% (individual reservoir data not shown).

The results obtained from this study show that the dual seal sample plate can be used to buffer exchange highly concentrated protein samples, as well as buffer exchange the samples with minimal loss of the sample protein.

The invention claimed is:

1. A sample plate for automated exchange of a buffer solution from a biological sample comprising:
    a plurality of reservoirs, wherein each reservoir of the plurality of reservoirs comprises a side wall, a ring shaped inner ridge, a filter attachment region comprising a thermal seal and an adhesive seal, and a ring shaped channel defined by the side wall and the ring shaped inner ridge, wherein the ring shaped channel comprises the thermal seal and is filled with an adhesive of the adhesive seal; and
    a filter having a diameter configured to accommodate a height of the ring shaped inner ridge so that a peripheral edge of the filter may be secured to each reservoir at the filter attachment region,
    wherein the filter attachment region maintains fixation of the filter peripheral edge to each reservoir at a pressure differential across the filter of at least about 30 psig.

2. The sample plate of claim 1, wherein the pressure differential across the filter is at least about 45 psig.

3. The sample plate of claim 1, wherein the pressure differential across the filter is at least about 60 psig.

4. The sample plate of claim 1, wherein the filter peripheral edge has a folded configuration, and the thermal seal and the adhesive seal secure the filter peripheral edge in its folded configuration to each reservoir.

5. The sample plate of claim 1, wherein the inner ridge of the reservoir has a height of about 0.38 mm.

6. A method for automated exchange of buffer solutions from a biological sample comprising:
    placing a sample plate comprising a plurality of reservoirs into a pressure chamber, wherein each reservoir of the plurality of reservoirs comprises a filter, and a filter attachment region comprising a thermal seal and an adhesive seal, and a ring shaped channel defined by a side wall and a ring shaped inner ridge of each reservoir, wherein the ring shaped channel comprises the thermal seal and is filled with an adhesive of the adhesive seal, and wherein the filter has a diameter configured to accommodate a height of the ring shaped inner ridge so that a peripheral edge of the filter may be secured to each reservoir at the filter attachment region; and
    pressurizing a space in the pressure chamber above the reservoir plate to generate a pressure differential across the filter of at least about 30 psig to separate the biological sample from a first buffer solution.

7. The method of claim 6, wherein the pressure differential across the filter is at least about 45 psig.

8. The method of claim 6, wherein the pressure differential across the filter is at least about 60 psig.

9. The method of claim 6, further comprising adding a second buffer solution to the plurality of reservoirs.

10. A method of manufacturing a sample plate for automated exchange of buffer solutions comprising:
    loading a filter having a peripheral edge into a plurality of reservoirs, wherein each reservoir of the plurality of reservoirs comprises a side wall, a ring shaped inner ridge, and a filter attachment region comprising a ring shaped channel defined by the side wall and the ring shaped inner ridge, wherein the filter has a diameter configured to accommodate a height of the ring shaped inner ridge so that the peripheral edge of the filter may be secured to each reservoir at the filter attachment region;
    thermally sealing the filter peripheral edge to the filter attachment region;
    filling the ring shaped channel with an adhesive; and
    curing the adhesive to adhesively seal the filter peripheral edge to the filter attachment region;
    wherein the filter attachment region maintains fixation of the filter peripheral edge to each reservoir at a pressure differential across the filter of at least about 30 psig.

11. The method of claim 10, wherein thermally sealing comprises applying heat and pressure to the filter peripheral edge such that the filter peripheral edge is secured to the inner ridge of each reservoir.

12. The method of claim 11, wherein the filter peripheral edge is folded against the inner ridge.

* * * * *